United States Patent
Türk

Patent Number: 6,159,193
Date of Patent: Dec. 12, 2000

[54] INJECTION SET

[76] Inventor: Rudolf Türk, Uppenbornstrasse 22a, Munich D-81735, Germany

[21] Appl. No.: 09/186,235

[22] Filed: Nov. 4, 1998

[30] Foreign Application Priority Data

Nov. 7, 1997 [DE] Germany ........................ 297 19 826 U
Sep. 7, 1998 [DE] Germany ........................ 298 16 077 U

[51] Int. Cl.$^7$ ................................................ A61M 37/00
[52] U.S. Cl. ............................................ 604/411; 604/414
[58] Field of Search ..................................... 604/187, 207, 604/208, 411, 415, 905, 263, 272; 141/27

[56] References Cited

U.S. PATENT DOCUMENTS

| | | | |
|---|---|---|---|
| 4,161,949 | 7/1979 | Thanawalla | 604/411 |
| 4,473,094 | 9/1984 | Harris | 604/411 |
| 4,981,464 | 1/1991 | Suzuki | 604/415 |
| 4,997,429 | 3/1991 | Dickerhoff et al. | 604/411 |
| 5,584,819 | 12/1996 | Kopfer | 604/239 |
| 5,807,374 | 9/1998 | Caizza et al. | 604/411 |
| 5,820,621 | 10/1998 | Yale et al. | 604/411 |
| 5,919,182 | 7/1999 | Avallone | 604/411 |

*Primary Examiner*—John G. Weiss
*Assistant Examiner*—David J. Cho
*Attorney, Agent, or Firm*—Schmeiser, Olsen & Watts

[57] ABSTRACT

The invention relates to an injection set (10) including at least one sterilized injection needle (18) and at least one needle protection sleeve (16) slipped onto each such needle, the injection set (10) additionally containing at least one small tube (24) as a syringe filling aid, with each tube (24) being attachable to an outer taper (44) each of a point (26) of a medical syringe (28).

19 Claims, 3 Drawing Sheets

INJECTION SET

FIELD OF THE INVENTION

The invention relates to an injection set containing at least one sterilized injection needle as well as at least one needle protection sleeve slipped thereon.

BACKGROUND OF THE INVENTION AND PRIOR ART

Conventional injection sets each contain one sterilized injection needle and one needle protection sleeve slipped on it. Injection sets for medical purposes are traditionally contained in an external wrapper, one part of which is usually made of swedged plastics and the other is a tear-open paper cover. Packed in this wrapper is the injection needle which consists of the sharpened metallic needle and the plastic connection piece with an inner taper which fits the outer taper of the syringe point. Slipped on said needle is an inflexible plastic sheath, the needle protection sleeve, which is to protect the needle point from damage and to prevent injuries.

If the doctor proceeds "lege artis", i.e. strictly according to the rules of the medical profession, he will first take the needle still bearing the slipped-on needle protection sleeve out of the packing, then take a syringe out of its packing, break open the ampulla containing the liquid to be injected, then fit needle onto the syringe, remove the needle protection sleeve, fill the syringe with the ampulla contents via the needle, discard the used needle, take a new needle out of its packing, fit the needle and its protection sleeve onto the syringe, remove the protection sleeve and inject the syringe contents.

Besides this approach which is the proper technique according to the rules of the medical profession, several improper variants are also used which all have the following in common: While, on the one hand, they involve great health risks and are impractical, they are nevertheless time- and cost-saving on the other hand:

In a first variant, the needle used for filling the ampulla contents into the syringe is also used for the actual injection. This method has two disadvantages. First of all, if it is required to use a relatively thin injection needle, filling frequently not very fluid ampulla contents into a syringe is very time-consuming and cumbersome. Secondly, the needle point, which is very soft, will frequently become deformed upon contact with the ampulla bottom, a fact which will often go unnoticed by the doctor. As a result, the injection will clearly be more painful for the patient because considerably more structures in the fatty tissue of the skin and in the muscles, to some extent also nerve fibers or blood vessels, will be damaged both when the needle is inserted and when it is pulled out again. The greater extent of damage to the body tissue thus also involves a higher risk of bleedings as well as of injection abscesses and of a retrogradely intravascular application.

In a second variant, no needle is used for filling the ampulla contents into the syringe but the ampulla contents are sucked directly into the syringe via the syringe point. This approach holds a great health risk for the patient. This is due to the shortness of the syringe taper which only extends half a centimeter into the ampulla for which reason the ampulla has to be tilted together with the syringe to cause the ampulla contents to flow to the open end of the ampulla. Often a drop of the ampulla contents will exit the open end of the ampulla despite the fact that the syringe is filled at the same time. Such drop will adhere to the non-sterile ampulla exterior and, when the ampulla is tilted further at the end of the syringe filling operation, will eventually also be sucked into the syringe.

From a hygienic point of view, this is a severe mistake of the doctor which is at the root of the majority of injection abscesses with their fatal consequences. Nevertheless, statistics have shown that this method is more common among doctors and medical staff than the method according to the rules of the medical profession.

Consequently, it is the object of the present invention to provide an injection set of the aforementioned type which is of low cost and allows a perfectly hygienic use.

SUMMARY OF THE INVENTION

An injection set according to the invention additionally contains at least one small tube as a syringe filling aid, said one or plural tube(s) being attachable to one outer taper of a point of a medical syringe. After breaking open the injection set only a little bit, the doctor will as a first step insert the taper of the syringe point into the tube which is elastic and will thus sit tightly on the syringe taper, sealing it effectively. The needle itself will remain perfectly sterile if the syringe is used for removing the tube from the injection set. The actual filling of the syringe can then occur perfectly hygienically without tilting the ampulla, and the ampulla will thereby be emptied fast and completely due to the relatively large tube diameter compared to that of the injection needle. The invention makes use of the fact that an injection needle used for filling a syringe with the contents of an ampulla would have certain properties which are not required for this process, such as a sharpened stainless steel needle which is moreover bonded to a plastic taper in such a manner that even high injection pressures will be withstood. If a small tube is used for filling the syringe with the ampulla contents, the demands made on the filling means will be reduced to the essential.

Usually, the injection set according to the invention will comprise at least three elements contained within a common packing, namely the injection needle, the needle protection sleeve and the small tube as a filling aid. According to a further advantageous embodiment of the invention, however, it is also possible to provide the sterilized tube separately or together with the medical syringe in a sterile packing. If the tube comes separately, this will ensure a maximum degree of hygiene. If the tube is packed together with the medical syringe, and fitted on the syringe point, this will advantageously do away with the step of fitting the tube onto the medical syringe. This will prevent further possible contamination and save time. Also, the amount of packaging material is minimized in this way since the small tube is already contained in the packing of the syringe. It is also possible to provide the syringe within the packing of the injection set.

According to a further embodiment of the invention, the small tube is individually packed. It may therefore be contained within a syringe packing and wrapped in a plastic or paper sleeve which may be stripped off. This will prevent hygienic mistakes when the syringe packing is broken open since the small tube is additionally covered.

In another embodiment of the invention, the one or plural tube(s) is/are contained in a dispenser. Since this embodiment will spare the doctor the work of opening sterile individual packings and he will readily have a sterile filling tube at his disposal whenever he needs one, this is a particularly time-saving alternative.

In yet another embodiment of the invention, the small tube is deformable in the manner of a plastic drinking straw.

In this case, the small tube will have at least one bending fold. Bending folds of this kind will allow the tube to be bent by 180° so that the packing of the injection set, the individual packing or the syringe packing containing the small tube can be kept relatively small in size. Since the plastic is chosen to be elastic, the tube will sit well on the syringe taper and therefore seal it tightly. In this embodiment, the small tube will not adhere to the syringe taper as firmly as the connection piece of the injection needle does, making it easier to detach and reducing the risk of injuries in doing so. Moreover, the small tube will not have to be disposed of as potentially hazardous waste since the tube itself will neither present a danger of infection due to previous patient contact nor a danger of injury as in the case of the sharpened needle point.

The added costs for the small tube are very low since the material used for drinking straws, which is customary in commerce, meets the requirements made on the food chemistry and can thus also be used for the present purpose. It must be taken care, though, that the injection set is only sterilized after its completion, i.e. only after it has been packaged.

It has proven particularly advantageous to make the total length of the small tube essentially identical to that of the injection needle with slipped-on needle protection sleeve. In this way, the rigidity of the conventionally used needle protection sleeve is taken advantage of, which also protects the relatively elastic tube from damage. Moreover, no special packing, for example of hard plastic, will be required for the small tube.

However, it may also be envisaged to make the tube shorter in length than the injection needle plus needle protection sleeve. This will ensure that—once the tube has been taken out of the injection set—the needle protection sleeve together with the injection needle will safely be held in the injection set packing made of plastic and paper, i.e. it will not slide out, which would involve the danger of insterility. The protective effect of the relatively rigid needle protection sleeve will be maintained. For special applications, e.g. in combination with injection needles which are relatively short in length as required for their special field of use, for instance for subcutaneous injections, it is also conceivable to make the tube longer than the total length of the combination of injection needle and needle protection sleeve.

It may be envisaged to make the diameter of the tube constant over its entire length, said diameter being larger than or identical to the external diameter of the end of the syringe taper. However, it is also conceivable to provide a tapering tube diameter, in which case the tube diameter will taper from the one end intended for contact with a syringe taper to the opposite end, said tapering being continuous or in steps. Special applications may also justify making the diameter larger.

In an embodiment of the invention, the tube is made of transparent material. This will ensure that when the syringe is being filled with the ampulla contents, it can be seen whether or not the tube still contains injection liquid.

DESCRIPTION OF THE DRAWINGS

The following is a description of embodiments of the present invention with reference to the enclosed drawings, in which.

DESCRIPTION OF THE EMBODIMENTS

Figure 1:
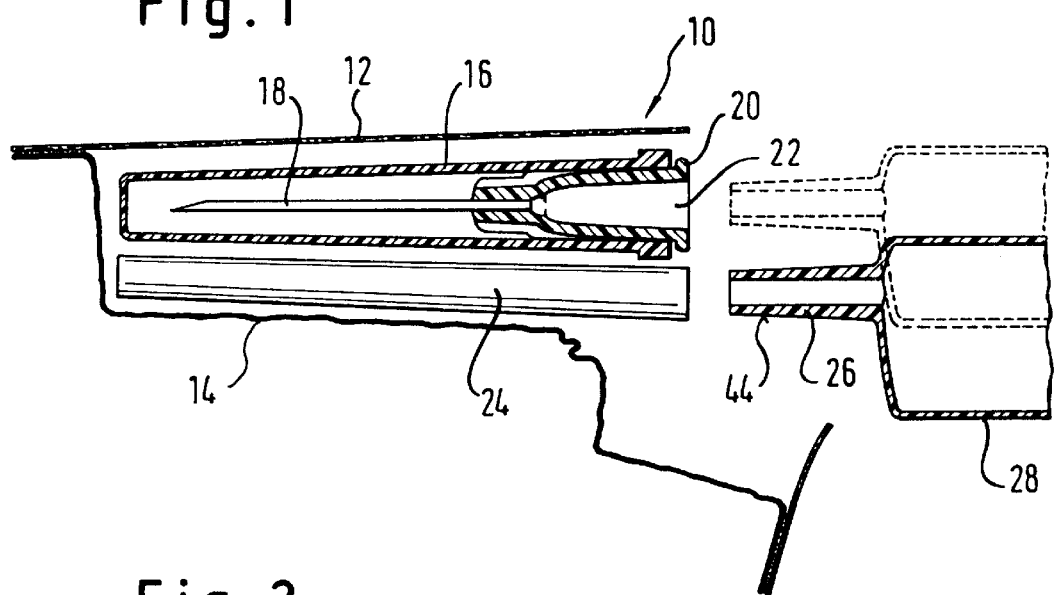
FIG. 1 is a schematical view of a first embodiment of an injection set according to the invention.

FIG. 1 is a schematical view showing an injection set, marked 10, according to the invention. The typical packing of injection sets consists of a paper rear wall 12 as well as a plastic film 14 shrunk-fit on the packing contents. However, it is also possible to create a recess for accommodating the contents of the injection set 10 therein by swedging a plastic material, and subsequently applying the rear wall 12 thereto in a further procedural step. The invention may be implemented with all packings known in this field.

The injection set traditionally comprises an injection needle 18 inserted in a needle protection sleeve 16 which is preferably made of inelastic plastic, said needle 18 including a connection piece 20 with an inner taper 22 at its end opposite the needle point. The needle point of the injection needle 18 is secured in the connection piece 20 in such a manner that it is capable of withstanding high injection pressures. The injection set 10 furthermore comprises a tube 24 as a syringe filling aid. Like the injection needle 18 plus connection piece 20, said tube 24 is sterile and preferably made of transparent plastic. In the illustrated embodiment, the diameter of the tube 24 tapers from the right-hand side of the drawing to the left. However, it can also be envisaged to make the tube 24 constant in diameter over its entire length. The diameter may be adjusted to the diameter of the ampulla neck. The tube 24 is of essentially the same length as the injection needle 18 with the needle protection sleeve 16 in place. The diameter of the tube 24 must be large enough to allow the tube to be slipped on an outer taper 44 of a syringe point 26 as is schematically shown in cross-sectional view in FIG. 1 or to allow the tube to accommodate the syringe point 26 in it. With regard to making the tube 24 sufficiently elastic, the wall thickness of the tube 24 must be selected in agreement with the material used for it.

However, the tube 24 may also be designed such that its diameter tapers from the end intended for contact with the syringe point 26 to the opposite end, in which case said tapering may be continuous or in steps. For special applications, for example for syringes having a very small diameter of the outer taper 44 or of the syringe point 26, it may also be envisaged to enlargen the diameter.

In the embodiment shown, the tube 24 rests directly on the needle protection sleeve 16 such that the rigidity of the needle protection sleeve 16 also protects the tube 24 from damage.

However, it may also be envisaged to add the tube 24 to a conventional injection set in a separate procedural step, in which case a plastic film (not shown) would be provided between the needle protection sleeve 16 and the tube 24. This will simultaneously ensure that, once the packing of the set 10 has been opened for use of the tube 24, whatever else is contained in the packing, i.e. the injection needle 18 with the needle protection sleeve 16, will remain sterile.

How the injection set is used properly: As shown schematically in FIG. 1, the outer taper 44 of the point 26 of the syringe 28 is first of all inserted in said tube 24 in a first step. Owing to the elasticity of the material used, preferably plastic, the tube 24 will sit reliably and tightly sealingly on the syringe point 26. The syringe point 26 with the tube 24 now slipped on is then used for sucking the contents of an ampulla containing the liquid to be injected into the hollow of the syringe 28. Thereafter, the tube 24 is removed from the syringe point 26 again. Since the tube 24 has neither contacted the patient nor does it exhibit a sharp edged point, this tube 24 may be disposed of without any problem. In particular, said tube 24 will not have to be disposed of as potentially hazardous waste.

In a second step, the point 26 of the syringe body 28 now filled with the ampulla liquid (see the dashed line view on the right at the top of FIG. 1) is inserted in the conventional way into the connection piece 20 of the injection needle 18 with the inner taper 22.

Once the injection needle 18 sitting on the syringe point 26 has been slid out of the needle protection sleeve 16, the doctor can inject the patient with the injection liquid.

Figure 2:
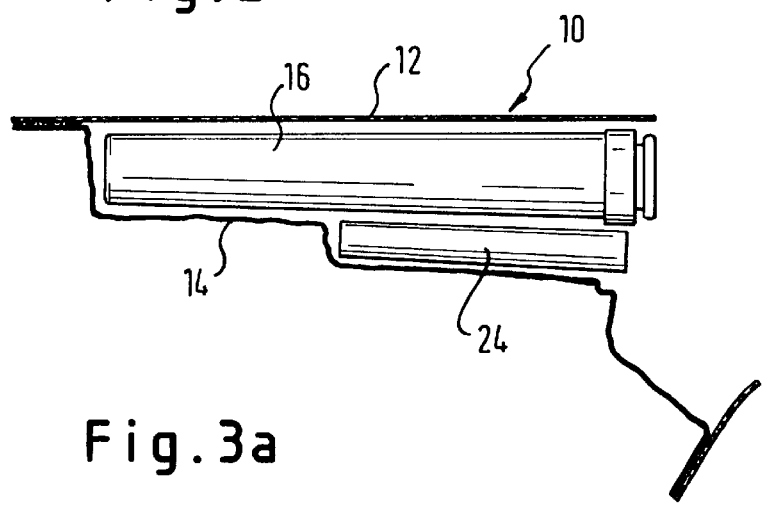
FIG. 2 is a schematical view of a second embodiment of an injection set according to the invention.

FIG. 2 shows another embodiment of the invention. In this view, just like in the ones following it, same reference numerals designate identical parts as in FIG. 1 for which reason these parts will not be described again.

In this embodiment the tube 24 is of a shorter total length than the combination of needle protection sleeve 16 and injection needle 18 of FIG. 1. This will ensure that even after the tube 24 has been removed from the injection set 10, the injection needle 18 plus needle protection sleeve 16 will reliably be held in the packing, and thus, when the injection set 10 is placed somewhere, the sterile components of the set 10 will not contact non-sterile objects surrounding them. The length of the tube 24 may be adjusted to the height of the ampulla containing the liquid to be injected.

Figure 3A:
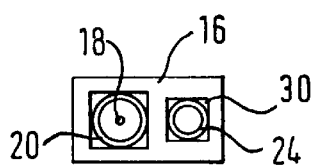
FIG. 3a is a top view of a needle protection sleeve for use in an injection set according to the invention.
Figure 3B:
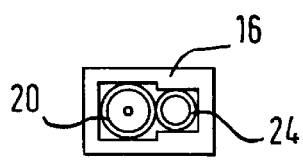
FIG. 3b is a top view of a further embodiment of a needle protection sleeve for use in an injection set according to the invention.

FIGS. 3a and 3b show embodiments in which the inventive thought has been developed further. While the view of FIG. 3a shows the needle protection sleeve 16 as having a further first chamber 30 for accommodating the tube 24, the variant shown in FIG. 3b has the two chambers, i.e. the one accommodating the injection needle 18 as well as the one accommodating the tube 24, spatially interconnected. The fact that a separate chamber is used for the tube 24 will safely prevent damage to the tube 24 during transport of the injection set 10.

In an embodiment not shown in the drawings, in order to ensure that the tube 24 will be securely held in the injection set 10 even after said set 10 has been opened, it is intended to use a spacer connected to the needle protection sleeve 16 of the injection needle 18—instead of a chamber for the tube 24. Said spacer may be in the form of a ring connected to the needle protection sleeve 16, preferably made of the same material as said needle protection sleeve, through which the tube 24 may be pulled before the contents of an ampulla are sucked into the syringe.

Figure 4:
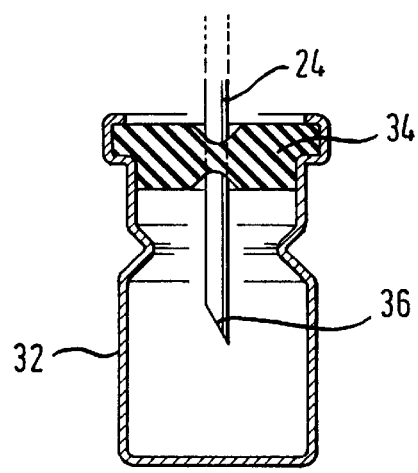
FIG. 4 is a schematical view of an embodiment of a tube for use in an injection set according to the invention.

FIG. 4 shows a particular embodiment of the tube 24 as it may for example be used for an ampulla 32 with a rubber plug 34. In this embodiment, the tube 24 has a point 36 which may be obtained in a simple manner by diagonally cutting the end of the tube 24. The material of the tube 24 will impart the latter a certain degree of rigidity to enable it to penetrate the rubber plug 34, preferably at places in the rubber plug 34 which are relatively thin, so as to suck the ampulla contents into the syringe 28.

Figure 5:
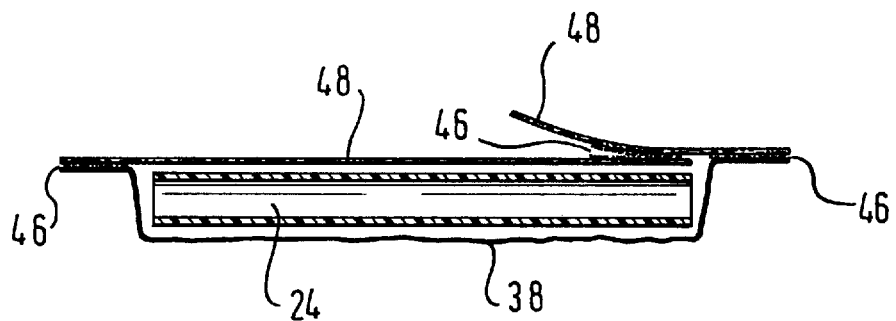
FIG. 5 is a schematical view of a tube for use in an injection set according to the invention, contained in an individual packing.
Figure 6:
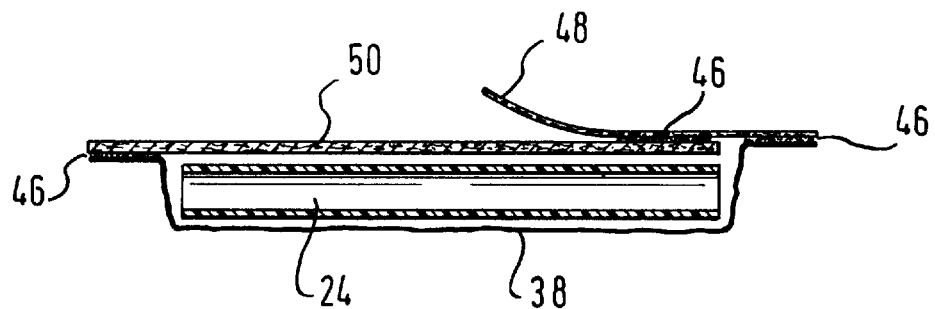
FIG. 6 is a schematical view of a tube for use in an injection set according to the invention, contained in a further individual packing.

FIG. 5 shows the tube 24 which is stored separately in a sterile individual packing 38. The individual packing 38 in this case is a plastic wrapper, in particular a unilaterally swedged soft plastic film. The plastic packing 38 forms a storage space for the tube 24 which is sealed off at its upward open side by means of a thin paper sheet 48. The paper sheet 48 is laterally bonded to adhesive portions 46 and thus detachably connected to the plastic packing 38. This results in a peelable individual packing. Since the tube 24 is individually packed, the paper side of the packing 38 must have a peelable doubling of the paper side or paper sheet 48 since the common breaking open of the paper sheet 48 will otherwise result in damage to the tube 24 because of its flexibility. A possible alternative is to provide one side of the packing 38 with an unfoldable reinforcement 50, as is shown in the view of FIG. 6, so as to protect the flexible tube 24.

Figure 7:
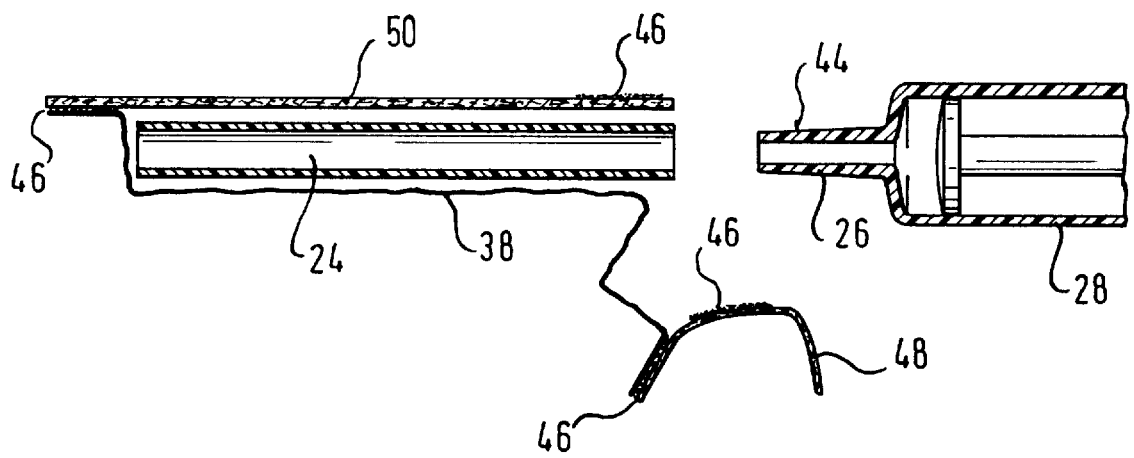
FIG. 7 is a schematical view of a tube for use in an injection set according to the invention, contained in an opened individual packing.

It may be gathered from the view of FIG. 7 how the individual packing 38 may be opened via the adhesive portions 46 which may be peeled apart and/or via the paper sheet 48 so as to expose part of the tube 24 for sliding one end thereof onto the outer taper 44 of the point 26 of the syringe 28. It can also be seen in this illustration that the predominant part of the tube 24 is still contained in the plastic packing 38 and is thus protected from contamination. The individual packings 38 described may also be used as a common container of the parts of the injection set 10, i.e. the injection needle 18, the needle protection sleeve 16 and the tube 24.

Figure 8:
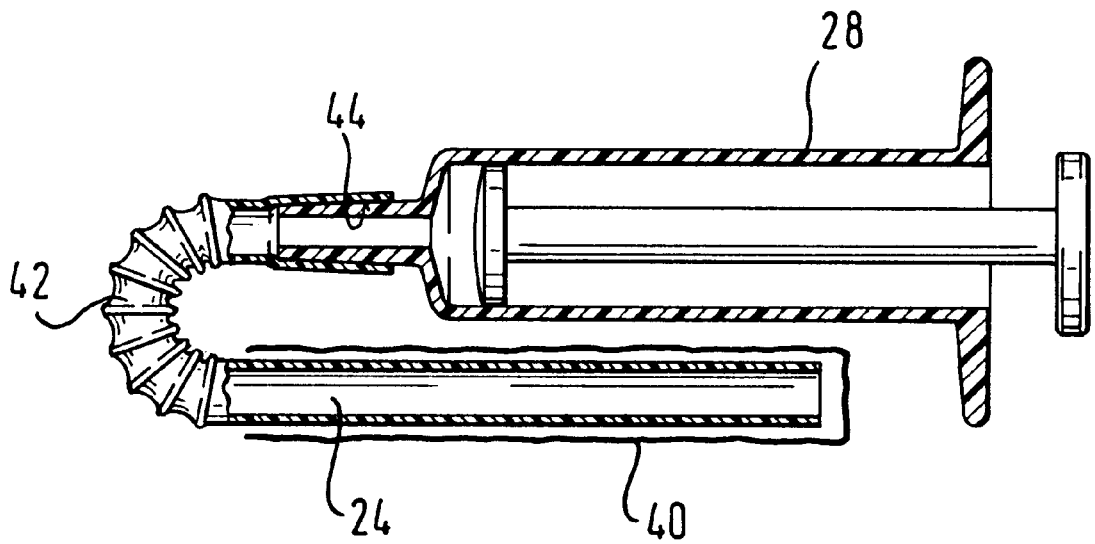
FIG. 8 is a schematical view of another embodiment of a tube for use in an injection set according to the invention.

Yet another embodiment of the tube 24 is shown in FIG. 8. One can see from this drawing that the filling tube 24 may be deformed like a plastic drinking straw and is provided with bending folds 42. The bending folds 42 may be bent by an angle of at least 180°. It may be gathered from this illustrated embodiment that the tube 24 already sits on the outer taper 44 of the point 26 of the syringe 28. Both parts are packed in a common syringe packing (not shown). It can further be seen that the straight portion of said tube 24 is provided with a sterile protection sleeve 40 which may be stripped off. Said protection sleeve 40 is taken out of the total packing (not shown) together with the syringe 28 and serves to keep the bending folds 42 straight for the syringe filling step without contaminating the tube 24. The protection sleeve 40 will then be stripped off immediately before the filling of the syringe 28.

Figure 9:
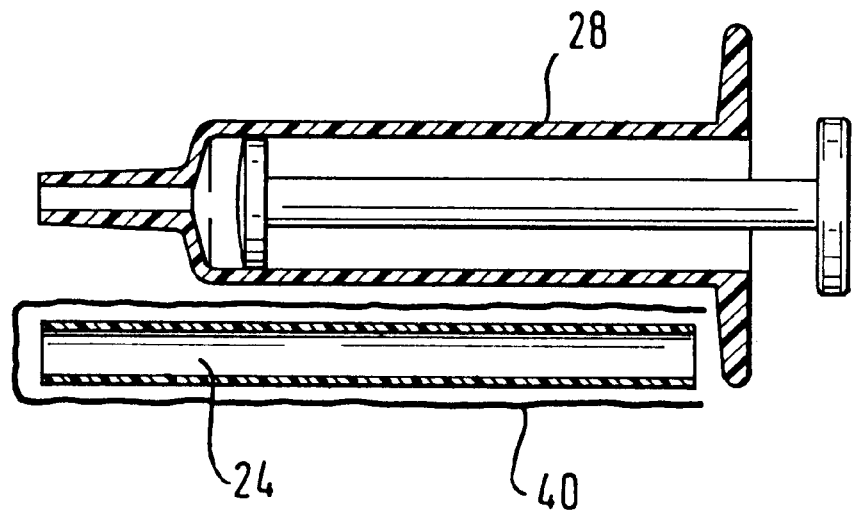
FIG. 9 is a schematical view of a further embodiment of a tube for use in an injection set according to the invention.

FIG. 9 likewise shows a tube 24 contained within a syringe packing (not shown). In this case, the tube 24 is surrounded by a protection sleeve 40. For preparing an injection, the doctor will break open the packing (not shown) and take out the syringe 28, subsequently inserting the outer taper 44 into the tube 24 still contained in the packing. Then he will strip off the protection sleeve 40 so that the contents of an ampulla may be filled into the syringe 28 by means of said tube 24.

What is claimed is:

1. The injection set including at least one sterilized injection needle and at least one needle protection sleeve slipped thereon wherein the injection set additionally includes at least one small tube as a syringe filling aid, the tube being attachable to an outer taper of a point of a medical syringe, and wherein the tube further rests longitudinally adjacent to the needle protective sleeve.

2. The injection set as claimed in claim 1 wherein the tube is stored in a sterile container either separately or together with the medical syringe.

3. The injection set as claimed in claim 2 wherein the tube is contained in an individual packing.

4. The injection set as claimed in claim 2 wherein the tube is contained within a syringe packing.

5. The injection set as claimed in claim 1 wherein the tube is provided with a plastic or paper protection sleeve which may be stripped off.

6. The injection set as claimed in claim 1 wherein the tube is contained in a dispenser.

7. The injection set as claimed in claim 1 wherein the tube may be deformed in the manner of a plastic drinking straw and includes at least one bending fold.

8. The injection set as claimed in claim 1 wherein the tube is of essentially the same length as the injection needle with the needle protection sleeve in place.

9. The injection set as claimed in claim 1 wherein the tube is shorter or longer than the combination of injection needle and needle protection sleeve.

10. The injection set as claimed in claim 1 wherein the diameter of the tube is constant over its entire length, said diameter being larger than or identical to the outside diameter of the end of the outer taper of the syringe point.

11. The injection set as claimed in claim 1 wherein the diameter of the tube tapers from the end intended for contact with the outer taper to the opposite end.

12. The injection set as claimed in claim 11 wherein the tube tapers continuously or in steps.

13. The injection set as claimed in claim 1 wherein the tube is transparent.

14. The injection set as claimed claim 1 wherein the tube rests is directly on the needle protection sleeve.

15. The injection set as claimed in claim 1 wherein there is a plastic film between the tube and the needle protection sleeve.

16. The injection set as claimed in claim 1 wherein one end of the tube has a point.

17. The injection set as claimed in claim 1 wherein the tube is fixed in position by a holding means in the injection set.

18. The injection set as claimed in claim 17 wherein said holding means is a second chamber formed in the needle protection sleeve.

19. The injection set as claimed in claim 17 wherein the holding means includes a holding ring which is connected to the needle protection sleeve.

* * * * *